(12) United States Patent
Whitsitt et al.

(10) Patent No.: US 10,373,712 B2
(45) Date of Patent: Aug. 6, 2019

(54) AGGREGATION, PARTITIONING, AND MANAGEMENT OF HEALTHCARE DATA FOR EFFICIENT STORAGE AND PROCESSING

(71) Applicant: CERNER INNOVATION, INC., Kansas City, KS (US)

(72) Inventors: Greg Whitsitt, Lee's Summit, MO (US); Micah Whitacre, Olathe, KS (US); Andrew Olson, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 14/707,627

(22) Filed: May 8, 2015

(65) Prior Publication Data

US 2015/0302149 A1 Oct. 22, 2015

Related U.S. Application Data

(63) Continuation-in-part of application No. 14/258,338, filed on Apr. 22, 2014.

(51) Int. Cl.
*G16H 10/60* (2018.01)
*G06F 19/00* (2018.01)

(52) U.S. Cl.
CPC ............ *G16H 10/60* (2018.01); *G06F 19/00* (2013.01)

(58) Field of Classification Search
CPC ................ G06Q 50/22–24; G06F 19/322–327
See application file for complete search history.

(56) References Cited

U.S. PATENT DOCUMENTS

| | | | | |
|---|---|---|---|---|
| 2002/0032583 A1* | 3/2002 | Joao | ...... | G06F 19/322 705/2 |
| 2005/0071194 A1* | 3/2005 | Bormann | ...... | G06F 17/30578 705/2 |
| 2007/0061393 A1 | 3/2007 | Moore | | |
| 2007/0162308 A1* | 7/2007 | Peters | ...... | G06F 19/328 705/2 |
| 2013/0304506 A1* | 11/2013 | Gallivan | ...... | G06Q 50/24 705/3 |

OTHER PUBLICATIONS

First Action Interview Office Action dated Aug. 25, 2016 in U.S. Appl. No. 14/258,338, 3 pages.
(Continued)

*Primary Examiner* — Robert A Sorey
(74) *Attorney, Agent, or Firm* — Shook Hardy & Bacon LLP

(57) ABSTRACT

Methods, systems, and computer-readable media are provided for aggregating, partitioning, and storing healthcare data. Healthcare data is collected from various disparate healthcare data sources. The data is aggregated into batches of the same type of data. From here, the data is partitioned according to the data's originating healthcare data source. The aggregated and partitioned healthcare data is then stored in a long term storage data store. This system of storing healthcare data allows for efficient retrieval and processing by computing solutions that need access to batches of healthcare data. The system also reduces costs associated with storing data as duplicate storage is eliminated.

18 Claims, 13 Drawing Sheets

(56) References Cited

OTHER PUBLICATIONS

First Action Interview Pilot Program Pre-Interview Communication dated Feb. 2, 2016 in U.S. Appl. No. 14/258,338, 5 pages.
First Action Interview Pilot Program Pre-Interview Communication dated Feb. 12, 2012 in U.S. Appl. No. 14/812,689, 4 pages.
First Action Interview Office Action dated Jun. 21, 2016 in U.S. Appl. No. 14/812,689, 5 pages.
Non-Final Office Action dated Dec. 15, 2017 in U.S. Appl. No. 14/812,689, 18 pages.
Final Office Action dated Jul. 11, 2018 in U.S. Appl. No. 14/812,689, 17 pages.

* cited by examiner

AGGREGATION, PARTITIONING, AND MANAGEMENT OF HEALTHCARE DATA FOR EFFICIENT STORAGE AND PROCESSING

CROSS REFERENCE TO RELATED APPLICATIONS

This application is a Continuation-In-Part application of copending U.S. patent application Ser. No. 14/258,338, filed Apr. 22, 2014, entitled "Synchronization of Healthcare Data Across Disparate Data Centers." This application is incorporated by reference in its entirety.

BACKGROUND

Computing platforms that ingest and process healthcare data face a number of challenges. For example, there has been a dramatic increase in the number of computer application solutions that utilize healthcare data to generate outcome data that is relevant to clinicians and patients. Locating the processing nodes that execute these solutions close to where the healthcare data is ingested and stored may be unfeasible as the healthcare data sets expand into the petabyte range. Co-locating the processing nodes with the underlying healthcare data may also be unfeasible due to physical size constraints of the data centers that host the nodes and/or rack availability at these data centers. As a result, processing nodes that subscribe to certain sets of healthcare data may not always be located at the data center where the healthcare data is received and stored.

This scenario may create a number of different problems. For example, a computing solution that utilizes a defined set of healthcare data from a healthcare data source may be located at a first data center, and another solution that requires the same set of healthcare data may be located at a second geographically-disparate data center. In this case, a crawler would need to pull the set of healthcare data from the healthcare data source twice, with one upload occurring at the first data center and a second upload occurring at the second data center. This process consumes valuable processing resources and Internet bandwidth at the healthcare data source. It is also duplicative and increases data center hosting costs. In another example, a new computing solution may be deployed at a data center, but the healthcare data needed by this new solution may be located at a different data center. In a typical case, the healthcare data would have to be re-extracted from the data source which once again consumes computing resources at the data source and increases data center hosting costs.

Another challenge faced by healthcare operating platforms is the loss of healthcare data due to, for example, a natural or man-made disaster occurring at the data center hosting the data. Because modern-day medicine relies heavily on the use of computer applications to aid decision making, loss of data hosted at a data center can significantly impair the healthcare delivery process. This problem becomes even more critical when the data that is lost is no longer available from the data's source.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to methods, systems, and computer-readable media for synchronizing healthcare data across multiple, disparate data centers. Healthcare data sources such as, for example, healthcare organizations upload their data to a data collector service that is part of a cloud computing platform. The data collector service acts as a front door to any number of different data centers. As the data collector service receives the healthcare data it is placed in a staging platform associated with a first data center that is hosting the collector service. The staging platform comprises durable, short-term storage (e.g., a durable cache) which allows for quick access to the healthcare data. Moreover, the data is durably replicated across multiple servers in the staging platform such that the failure or loss of an individual staging platform server does not result in the data being lost. Additionally, the data is indexed such that it is available for low-latency processing.

Once the data is in the staging environment, it is stored in a long-term storage data store associated with the first data center; this data store is optimized for long-term storage of healthcare data. As well, it is determined if any processing nodes at the first data center subscribe to or utilize the received healthcare data when implementing its solutions. If so, the data is communicated to those processing nodes where it is subsequently processed to generate clinically-relevant outcomes.

In addition, the data is communicated to a staging platform associated with a second data center. The staging platform stores the healthcare data in a long-term storage data store associated with the second data center and also may communicate the data to any processing nodes at the second data center that subscribe to the data. Storing the received healthcare data in long-term storage data stores associated with disparate data centers facilitates data recovery in the event that one of the data centers is compromised by, for example, a natural or man-made disaster. Moreover, efficiently delivering the data to those data centers and processing nodes that have expressed an interest in the data eliminates the need to re-crawl the healthcare data source for the needed data.

BRIEF DESCRIPTION OF THE DRAWINGS

Embodiments are described in detail below with reference to the attached drawing figures, wherein.

DETAILED DESCRIPTION

Figure 1:
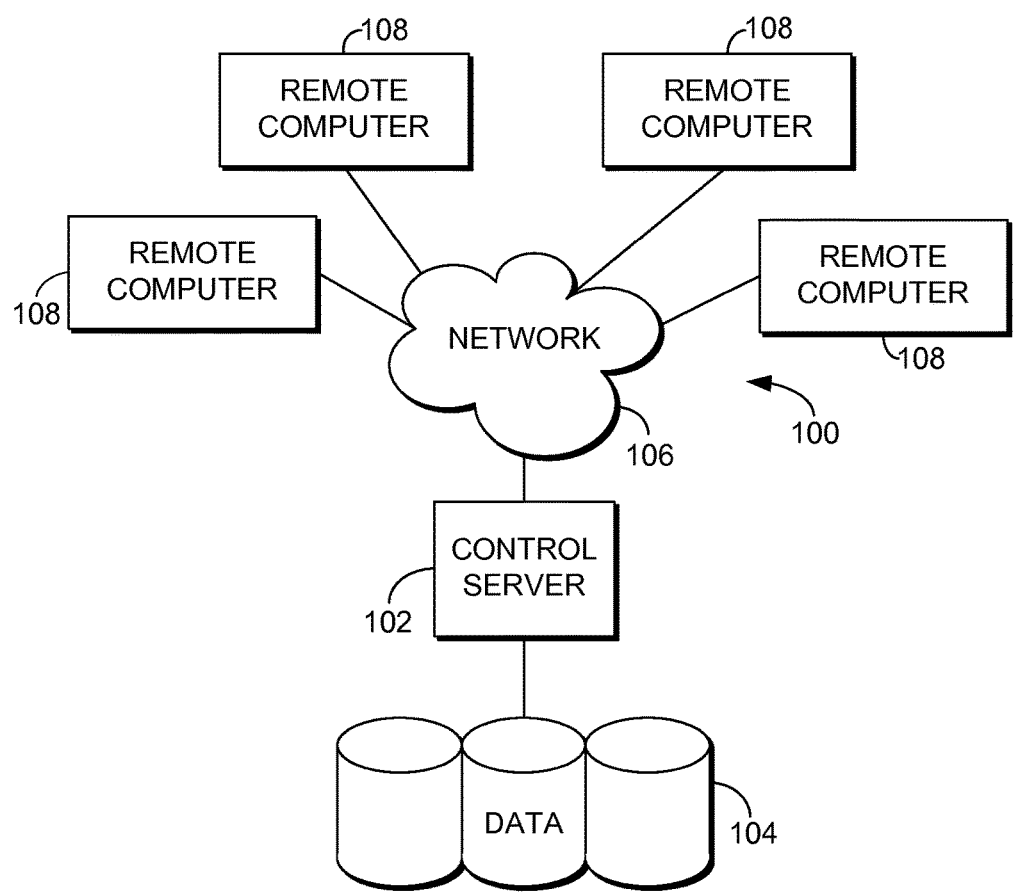
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for synchronizing healthcare data across multiple, disparate data centers. A data collector service associated with a cloud computing platform receives healthcare data from one or more healthcare data sources. Once received, the data is sent to a staging platform associated with a first data center. The staging platform stores the healthcare data such that it can be quickly accessed, and it also indexes the data so that is optimized for low-latency (e.g., real-time) processing. The staging platform also stores the healthcare data in a long-term storage data store associated with the first data center. The long-term storage data store is optimized to store the healthcare data for long periods of time, potentially never deleting the data. This is useful in the event that the data is needed at a future point of time (i.e., when implementing a new computing solution) and obviates the need to re-crawl the data's source to obtain the needed data.

Additionally, the staging platform communicates the healthcare data to any processing nodes associated with the first data center that subscribe to or utilize the data. These processing nodes may perform either batch processing or low-latency processing on the data, depending on the nature of the computing solution implemented by the particular node. In the event a processing node is performing batch processing of the data, the staging platform is configured to store the data in the long-term storage data store until it is needed by the node. In the event a processing node is performing low-latency processing on the healthcare data, the staging platform is configured to immediately communicate the received healthcare data to the node.

As well, the staging platform associated with the first data center is configured to communicate the received healthcare data to a staging platform associated with a second data center where it is subsequently stored in a long-term storage data store associated with the second data center. This process ensures that the data is stored in at least two geographically-disparate data centers in the event that the data is corrupted or destroyed at one of the data centers. The staging platform associated with the second data center may further communicate the data to processing nodes associated with the second data center that utilize or subscribe to the healthcare data. Once the healthcare data has been stored in at least two long-term storage data stores associated with disparate data centers, and once the healthcare data has been communicated to all the processing nodes that subscribe to the data regardless of where the processing nodes are physically located, the healthcare data stored by the staging platforms may be removed or deleted so as to free up storage or cache space for new incoming healthcare data.

The cloud computing platform described above not only provides full disaster recovery capabilities, but also effectively moves healthcare data closer to the processing nodes that subscribe to the data—even if those processing nodes are located at geographically-disparate data centers. Additionally, the cloud computing platform described above enables a particular healthcare data source to upload a particular piece of data a single time to the platform as opposed to, for example, having to upload the particular piece of data to each of the data centers that utilize the data. This saves the healthcare data source valuable processing resources and Internet bandwidth, and reduces data center hosting costs.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
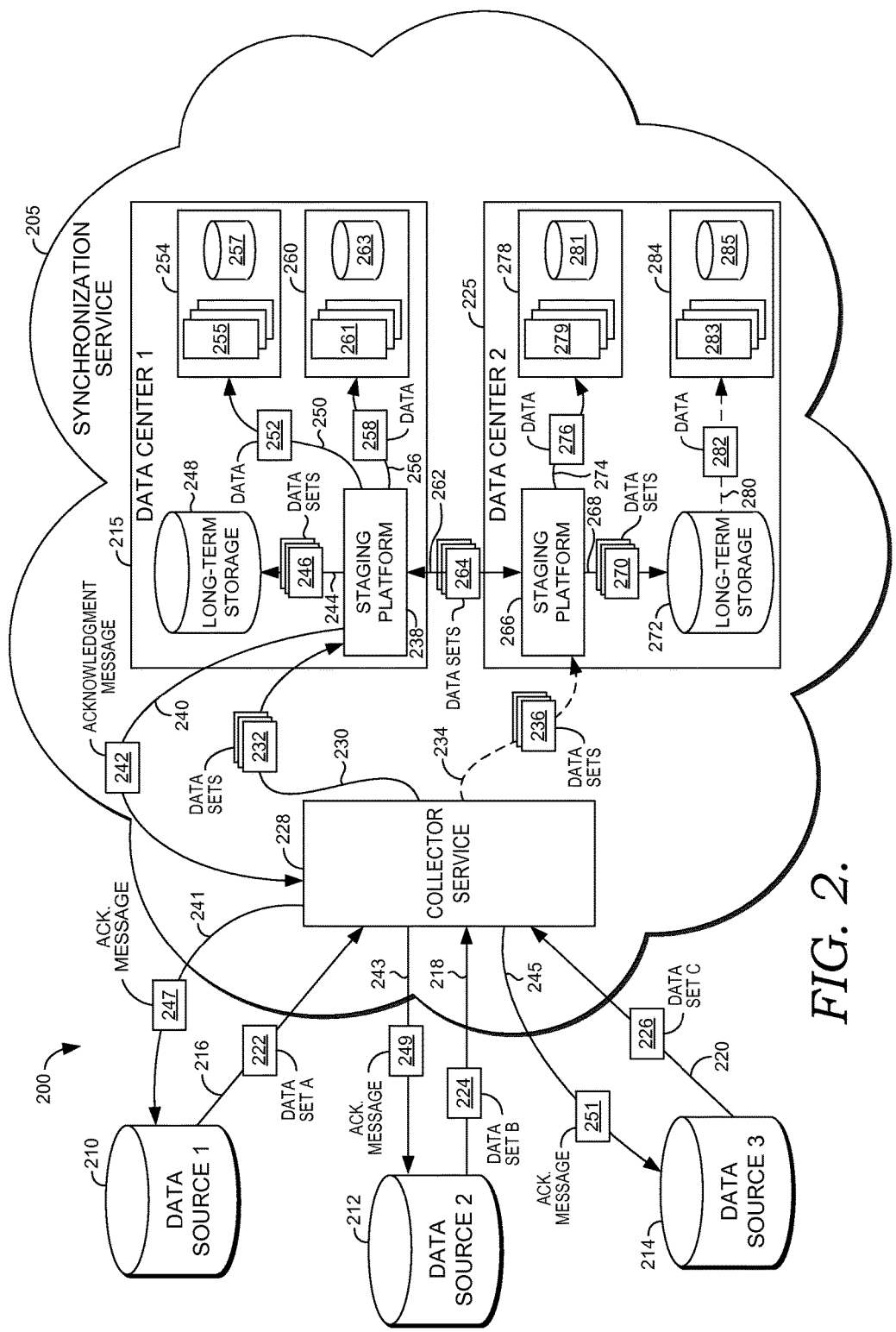
FIG. 2 is a block diagram of an exemplary system for synchronizing healthcare data across multiple, disparate data centers suitable to implement embodiments of the present invention.

Turning now to FIG. 2, a block diagram 200 is illustrated, in accordance with an embodiment of the present invention, showing an exemplary synchronization service 205 implemented in a cloud computing platform. It will be understood and appreciated that the cloud computing platform shown in FIG. 2 is merely an example of one suitable computing system environment and is not intended to suggest any limitation as to the scope of use or functionality of embodiments of the present invention. For instance, the cloud computing platform may be a public cloud, a private cloud, or a dedicated cloud. Neither should the cloud computing platform be interpreted as having any dependency or requirement related to any single component or combination of components illustrated therein. Further, although the various blocks of FIG. 2 are shown with lines for the sake of clarity, in reality, delineating various components is not so clear, and metaphorically, the lines would more accurately be grey and fuzzy. In addition, any number of physical machines (such as computing devices or portion of computing devices 108 shown in FIG. 1), virtual machines, data centers, endpoints, or combinations thereof may be employed to achieve the desired functionality within the scope of embodiments of the present invention. As mentioned, the cloud computing platform comprises a cloud-computing network, which is known in the art as "the cloud."

As shown in FIG. 2, the synchronization service 205 is capable of communicating with a number of different entities or data sources such as the healthcare data sources 210, 212, and 214 for the collection of healthcare data. This communication may utilize, without limitation, one or more local area networks (LANs) and/or wide area networks (WANs). Such networking environments are commonplace in offices, enterprise-wide computer networks, intranets, and the Internet. Accordingly, the network is not further described herein. As used throughout this application, the term "healthcare data" is meant to be broad and encompass any type of healthcare information. The healthcare data may be specific to a single patient or a group of patients. The healthcare data may also be directed to a clinician or group of clinicians. For example, healthcare data as it relates to a clinician may include patients that the clinician treats.

The healthcare data sources 210, 212, and 214 may include, for example, a hospital, a physician's office, a health information exchange, an urgent care clinic, and the like. Healthcare data received from these different sources 210, 212, and 214 may include, but is not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information.

It should be noted that the healthcare data sources 210, 212, and 214 shown as communicating with the synchronization service 205 in FIG. 2 are provided by way of example only and are not intended to limit the scope of the present invention in any way. Each healthcare data source 210, 212, and 214 may have one or more computing devices such as computing device 108 of FIG. 1, for communicating with the synchronization service 205. Each healthcare data source 210, 212, and 214 may maintain its own native electronic medical record (EMR) system. Further, the healthcare data sources 210, 212, and 214 may be disparate from each other such that the data sources 210, 212, and 214 are not directly connected with one another. In one aspect, the healthcare data sources 210, 212, and 214 send information to the synchronization service 205 and not typically directly between one another.

Further, the healthcare data sources 210, 212, and 214 may be able to access the synchronization service 205 in a variety of ways within the scope of the present invention. For example, in some embodiments, a healthcare data source may have a native clinical computing system, which may be able to communicate with the synchronization service 205. In other embodiments, a client application associated with the synchronization service 205 may reside or partially reside on one or more of the healthcare data sources' computing devices facilitating communication with the synchronization service 205. In further embodiments, communication may simply be a web-based communication, using, for example, a web browser to communicate with the synchronization service 205 via the Internet. Any and all such variations are contemplated to be within the scope of embodiments of the present invention.

As shown in FIG. 2, the synchronization service 205 comprises a collector service 228, a first data center 215, and a second data center 225. The collector service 228 is configured to receive or extract healthcare data from each of the data sources 210, 212, and 214 as either a stream of data and/or in batches. The collector service 228 collects the healthcare data by one of several methods. For instance, the collector service 228 may include, in one aspect, a program that extracts relevant data from the data sources 210, 212, and 214. For example, the collector service 228 may extract relevant healthcare data for a particular patient from the patient's EMR. The healthcare data may include a complete historical record of a patient's EMR along with any updates or modifications to the patient's EMR. Updates are received or extracted by the collector service 228 substantially simultaneously with when the information is updated in the patient's EMR. In another aspect, the collector service 228 may query the data sources 210, 212, and 214 to obtain patient information. In yet another aspect, the healthcare data sources 210, 212, and 214 may utilize a Web interface to upload their data.

The collector service 228 spans multiple data centers such as the data center 215 and the data center 225. In other words, the collector service 228 acts as a "front door" that receives healthcare data from the different sources 210, 212, and 214 without regard to which data center will eventually process the data. From the perspective of the data sources 210, 212, and 214, these data sources simply upload their data to the collector service 228 instead of having to upload their data to each of the data centers (e.g., the data centers 215 and 225) that will eventually process their data. In one exemplary aspect, the collector service 228 may be available to each of the data sources 210, 212, and 214 through a Web interface. Each data source 210, 212, and 214 is provided with a uniform resource locator (URL) (e.g., a URL referencing the collector service 228) by which to upload the healthcare data. Because of the characteristics of the synchronization service 205, which will be explained in greater depth below, a single piece of healthcare data need only be uploaded once to the collector service 228. The piece of healthcare data does not have to be re-uploaded in the event of, for example, physical loss of data at one of the data centers 215 or 225, or the introduction of a new computing solution at one of the data centers 215 or 225 that utilizes the particular piece of data.

As mentioned, the synchronization service 205 further includes the data center 215 and the data center 225. The data centers 215 and 225 are contemplated as being located in geographically-disparate locations. Although only two data centers are depicted in FIG. 2, it is contemplated that the synchronization service 205 may include multiple, geographically-disparate data centers. In general, only one data center hosts the collector service 228 at any given time, although any of the data centers associated with the synchronization service 205 are capable of hosting the collector service 228. As shown in FIG. 2, the data center 215 is currently hosting the collector service 228. What is meant by the term "hosting" will be explained in greater depth below.

Taking the data center 215 as a representative example, the data center 215 comprises at least a staging platform 238, a long-term storage data store 248, a first processing node 254, and a second processing node 260. The components associated with the data center 215 are equally applicable to the data center 225. Further, the descriptions of these various components are equally applicable to both the data center 215 and the data center 225 unless indicated otherwise.

As mentioned, the data center 215 is currently hosting the collector service 228. This means that healthcare data received by the collector service 228 from the data sources 210, 212, and 214 is communicated to the staging platform 238 associated with the data center 215. If the staging platform 238 is not available to receive the healthcare data from the collector service 228, then staging platform 266 associated with the data center 225 may be used to receive the data from the collector service 228.

The staging platform 238 comprises a durable cache that provides quick access to the healthcare data. Once healthcare data has been accepted into the staging platform 238, the data is durably replicated across multiple servers in the staging platform. Thus, the failure or loss of an individual staging platform server does not result in the data being lost. The staging platform 238 indexes the healthcare data in such a way that it is accessible for low-latency processing. As well, healthcare data stored in association with the staging platform 238 is generally categorized by source (e.g., data source 210, 212, or 214).

The staging platform 238 is optimized for several different functions. First, the staging platform 238 is configured to communicate an acknowledgment message to the collector service 228 once it has accepted the healthcare data; the collector service 228, in turn, communicates an acknowledgment message to each of the healthcare data sources 210, 212, and 214 acknowledging receipt of the data. The staging platform 238 is also configured to store the data in association with the long-term storage data store 248. The long-term storage data store 248 is configured to store the data for long periods of time, potentially never deleting the data. Healthcare data stored in the long-term storage data store 248 is generally stored as-is with the addition of metadata describing the data's source and when it was received. Data stored in association with the long-term storage data store 248 can be accessed for use by, for example, analytic workflows that may need to utilize data that was received months or even years ago. As well, data stored in association with the long-term storage data store 248 can also be accessed by new computing solutions implemented by processing nodes within the data center 215 or even by existing computing solutions that did not need the data at the time it was received.

Returning to the staging platform 238, the staging platform 238 is additionally configured to communicate the healthcare data to one or more of the processing nodes 254 and 260. With respect to this aspect, routing logic associated with the synchronization service 205 determines which processing nodes subscribe to or utilize the healthcare data. Based on this determination, the staging platform 238 communicates the healthcare data or subsets of the healthcare data to the appropriate processing node.

Further, the staging platform 238 is adapted to route the healthcare data to staging platforms associated with other data centers, such as the staging platform 266 associated with the data center 225. The determination of which data center(s) to route the healthcare data may be determined by the routing logic discussed above. For example, if it is determined that processing nodes associated with a particular data center(s) subscribe to the healthcare data, then the healthcare data is routed to this particular data center(s). In another example, if it is determined that the only processing nodes that are currently subscribing to the healthcare data are those associated with the data center 215, then the routing logic determines a data center located in a geographically-disparate location to which to communicate the healthcare data (where it is subsequently stored in the center's long-term storage data store to facilitate data recovery in disaster situations). It is contemplated that the staging platform 238 may communicate the healthcare data to multiple disparate data centers depending on whether processing nodes associated with those data centers subscribe to the data.

Once the healthcare data accepted by the staging platform 238 has been stored in association with the long-term storage data store 248, communicated to a staging platform associated with a disparate data center (such as the staging platform 266 associated with the data center 225), and communicated to those processing nodes that subscribe to the healthcare data (either processing nodes associated with the data center 215, processing nodes associated with disparate data centers, or both), the healthcare data may be deleted from the staging platform 238. This helps to ensure that sufficient cache space is available at the staging platform 238 for new incoming healthcare data.

The processing nodes 254 and 260 are each adapted to implement a healthcare solution. In some cases, these may be the same computing solution, and in other cases these may be different computing solutions. Although only two processing nodes are shown in association with the data center 215 and the data center 225, it is contemplated that each data center may comprise more than two processing nodes. Each processing node 254 and 260 includes, for example, a plurality of parallel processors, 255 and 261 respectively, and a storage engine 257 and 263 respectively. The storage engines 257 and 263 are configured to temporarily store the healthcare data utilized by the respective parallel processors 255 and 261. The parallel processors 255 and 261 may be optimized for batch processing and/or low-latency (e.g., real-time) processing depending on the healthcare solution implemented at the particular processing node. By way of illustrative example, the processing node 254 may implement a solution that provides clinicians with up-to-date views of patient data. As such, it performs low-latency processing on a generally continuous stream of healthcare data received, via the staging platform 238, from the data sources 210, 212, and 214. By contrast, the processing node 260 may implement a solution that analyzes outcomes associated with aggregated sets of healthcare data. A solution such as this does not generally require continually-updated information but may, instead, perform batch processing on data received every, for example 24 hours.

As described above, the processing nodes 254 and 260 may receive data from the staging platform 238. For low-latency processing, healthcare data at the staging platform 238 is indexed and immediately sent to the processing node executing the low-latency processing. In the event that a processing node associated with the data center 225 (e.g., the processing nodes 278 and/or 284) performs low-latency processing on the data, the staging platform 266 immediately communicates the needed data to the low-latency processors after it has received the data from the staging platform 238. The result of this is that data received from a data source is immediately available to processing nodes subscribing to the data regardless of whether the processing nodes are located at geographically-disparate data centers.

For batch processing, healthcare data at the staging platform 238 may be communicated to the storage engines associated with the processing nodes 254 and 260 (e.g., the storage engines 257 and/or 263). The storage engines 257 and/or 263 may store the healthcare data until it is needed by the processing node executing the batch processing. In another aspect, data needed for batch processing may be accessed from the long-term storage data store 248. In yet another aspect, the long-term storage data store 248 may be utilized as a storage engine for a particular processing node at the data center 215.

The healthcare data stored in association with the long-term storage data store 248 may also be accessed by the processing nodes 254 and 260 for different reasons. For example, this may occur when an existing data source (e.g., healthcare facility) requests enrollment in a computer solution implemented by one of the processing nodes 254 or 260. Instead of having to re-extract the data needed by this solution from the data source, the processing node 254 or 260 can simply access the data from the long-term storage data store 248. As well, this may occur when a new computing solution is added to the data center 215 that utilizes the healthcare data. Any and all such aspects, and any variation thereof, are contemplated as being within the scope of the invention.

Still with reference to FIG. 2, a process-flow will now be described to better illustrate the claimed invention. At a step 216, the data source 210 communicates a data set A 222 to the collector service 228. Likewise, at a step 218, the data source 212 communicates a data set B 224 to the collector service 228, and at a step 220, the data source 214 communicates a data set C 226 to the collector service 228. In each case, the data sources 210, 212, and 214 may, for example, utilize a URL to upload the data sets 222, 224, and 226 to the collector service 228. The data sets 222, 224, and 226 may comprise historical records of patients' EMRs, and/or they may comprise updates to data already stored in association with the synchronization service 205.

At a step 230, the collector service 228 communicates the data sets 222, 224, and 226 (labeled as data sets 232) to the staging platform 238 associated with the data center 215. The data collected from each of the data sources 210, 212, and 214 is kept separate. Alternatively, and as shown by the dashed arrow, if the data center 225 was hosting the collector service 228, the collector service 228 would, at a step 234, communicate the data sets 222, 224, and 226 (labeled as data sets 236) to the staging platform 266 associated with the data center 225.

Once the staging platform 238 receives the data sets 232 from the collector service 228, it communicates, at a step 240, an acknowledgment message 242 to the collector service 228. The collector service 228, in turn, communicates respectively at steps 241, 243, and 245, acknowledgement messages 247, 249, and 251 to each of the data sources 210, 212, and 214 acknowledging that the data sets 222, 224, and 226 have been accepted into the staging platform 238.

At a step 244, the staging platform 238 stores the data sets (now labeled as data sets 246) in association with the long-term storage data store 248 which persistently stores the data sets 246 to facilitate disaster recovery as well as to obviate the need for re-extraction from the data sources 210, 212, and 214 in the event that data within the data sets 246 is needed at a future point in time.

Based on the processing node 254 subscribing to some or all of the data contained in the data sets 232, the staging platform 238, at a step 250, communicates data 252 to the processing node 254 where it is subsequently processed to generate clinically-relevant information. The processing may be batch processing and/or low-latency processing conditioned on the nature of the computing solution hosted by the processing node 254. Depending on whether the data sources 210, 212, and 214 have enrolled in the solution hosted by the processing node 254, the data 252 may comprise some or all of the data sets communicated by the healthcare data sources 210, 212, and 214 to the synchronization service 205 (e.g., data sets 222, 224, and 226). As well, depending on the nature of the solution implemented by the processing node 254, a particular source's entire data set or a subset of the source's data set may be included in the data 252. Similarly, based on the processing node 260 subscribing to some or all of the data contained in the data sets 232, at a step 256, the staging platform 238 communicates data 258 to the processing node 260 where it is subsequently processed to generate clinically-relevant outcome data. In the event that each of the processing nodes 254 and 260 implements different solutions, the data 258 may differ from the data 252. If the processing nodes 254 and 260 implement the same solution, then the data 258 may be the same as the data 252. The step 250 may occur concurrently with the step 244 (e.g., the staging platform storing the data sets 246 in association with the long-term storage data store 248).

At a step 262, the staging platform 238 communicates the data sets (labeled as data sets 264) to the staging platform 266 associated with the data center 225. The arrow between the data centers 215 and 225 is shown as being bi-directional to indicate that if the data center 225 is hosting the collector service 228, the staging platform 266 would be communicating the data sets 264 to the staging platform 238 associated with the data center 215. The step 262 may occur concurrently with the steps 244, 250, and 256. After the staging platform 238 has completed these actions, the data sets 232 may be deleted from the staging platform 238 to free up cache space.

The determination of which disparate data center to communicate the data sets 264 may be based on, for example, whether processing nodes associated with the disparate data center subscribe to some or all of the data in the data sets 264, or, in the event that no further processing nodes subscribe to the data contained in the data sets 264, the determination may be based on the geographic location of the disparate data center (i.e., to facilitate disaster recovery, a data center located a predetermined distance away from the data center 215 may be selected).

Once accepted into the staging platform 266 of the data center 225, the staging platform 266 stores the data sets 264 in such a way that data within the data sets 264 is easily accessible. Further, it indexes the data in the data sets 264 to make it accessible for low-latency processing. At a step 268, the staging platform 266 stores the data sets (labeled as data sets 270) in association with the long-term storage data store 272 associated with the data center 225. As well, based on the processing node 278 subscribing to some or all of the data in the data sets 264, at a step 274, the staging platform 266 communicates data 276 to the processing node 278 which subsequently processes the data 276 (utilizing batch processing, low-latency processing, or a combination of both) to generate clinically-relevant outcome information. The data 276 may comprise some or all of the data in the original data sets 222, 224, and/or 226 received from the healthcare data sources 210, 212, and 214. The steps 268 and 274 may occur concurrently with each other.

As shown in FIG. 2, the staging platform 266, based on routing logic, does not communicate data to the processing node 284. This may be because the processing node 284 does not subscribe to the type of data contained in the data sets 264, or it may be because the healthcare data sources 210, 212, and 214 are not currently enrolled in the computing solution hosted by the processing node 284. However, if at a later point in time, one or more of the data sources 210, 212, and/or 214 enroll in the solution hosted by the processing node 284, the processing node 284 can access the needed data from the long-term storage data store 272. This is indicated in FIG. 2 by the dashed line 280 illustrating that data 282 is communicated to the processing node 284 from the long-term storage data store 272. Like the staging platform 238, once the staging platform 266 associated with the data center 225 carries out these steps, the healthcare data may be deleted from the staging platform 266.

Although the process-flow shown in FIG. 2 depicts data being communicated between two data centers, it is contemplated that the staging platform 238 associated with the data center 215 may communicate the data to multiple, disparate data centers. This may occur when processing nodes associated with each of the multiple, disparate data centers subscribe to the data accepted into the staging platform 238.

Figure 3:
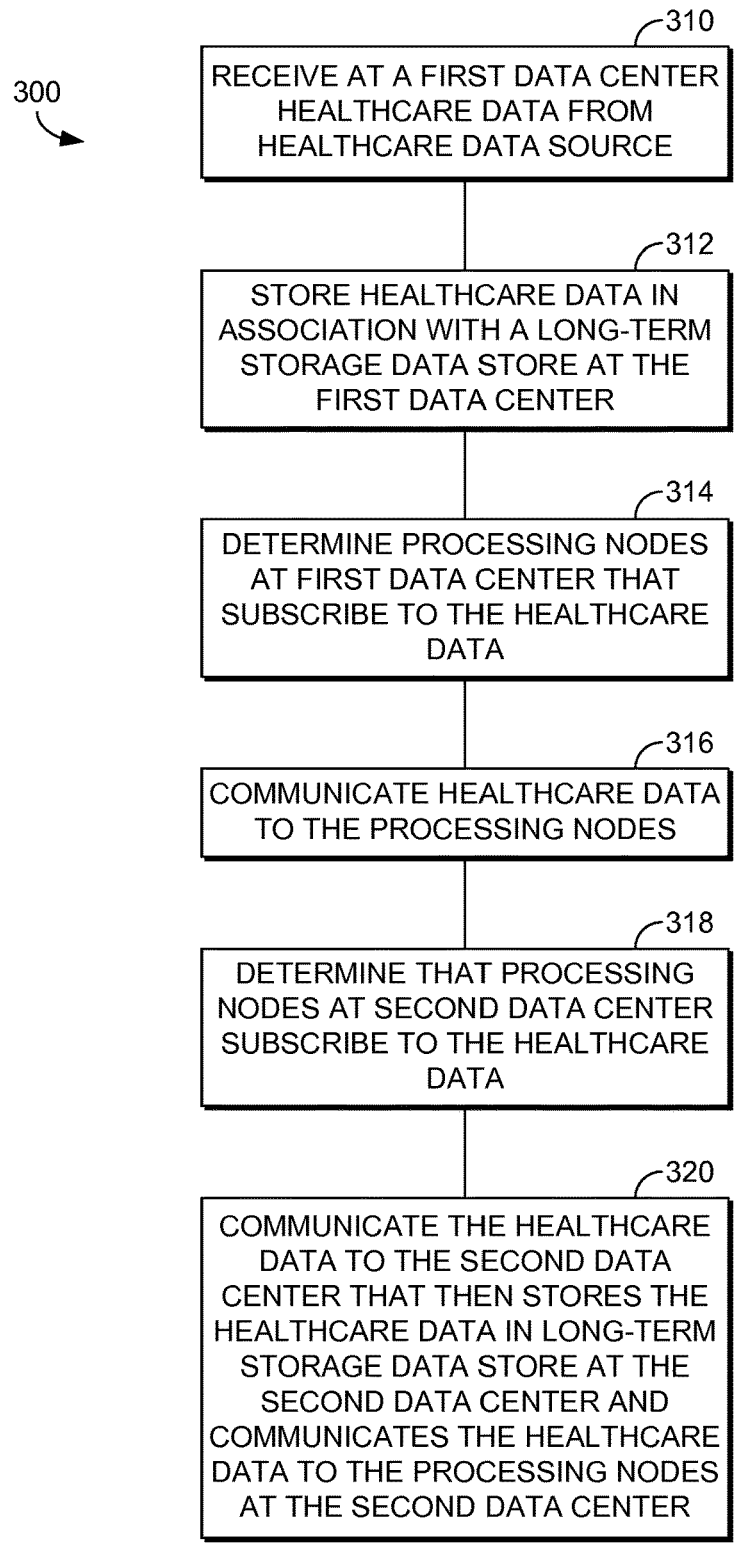
FIGS. 3-5 are flow diagrams of exemplary methods of synchronizing healthcare data across multiple, disparate data centers in accordance with embodiments of the present invention.

Turning now to FIG. 3, a flow diagram is depicted of an exemplary method 300 of synchronizing healthcare data across multiple data centers. Although the term "step" may be used herein to connote different elements of methods employed, the term should not be interpreted as implying any particular order among or between various steps herein disclosed unless and except when the order of individual steps is explicitly described.

The method 300 may be carried out by a synchronization service such as the synchronization service 205 of FIG. 2. At a step 310, healthcare data is received at a first data center from a healthcare data source such as, for example, a healthcare facility. The healthcare data may comprise historical EMR information and/or it may comprise updates to information already stored in association with the synchronization service. The data may be received as a continuous or substantially continuous stream of data, and/or the data may be received in batches. The healthcare data may be initially received by a collector service, such as the collector service 228 of FIG. 2 that acts as a "front door" to the first data center. From the collector service, the data is sent to a staging platform associated with the first data center, such as the staging platform 238 associated with the data center 215 of FIG. 2.

At a step 312, the healthcare data is stored in association with a long-term storage data store associated with the first data center, such as the long-term storage data store 248 of FIG. 2. In the event the healthcare data comprises an update to already-existing information in the long-term storage data store, the updated healthcare data is stored as a new version. The long-term storage data store persistently stores the data and makes it available in the event of, for example, disaster recovery, implementation of a new computing solution, and/or an existing processing node needing the data at a later point in time.

At a step 314, one or more processing nodes associated with the first data center (such as the processing nodes 254 and 260 of FIG. 2) that subscribe to the healthcare data are determined. The determination may be based on routing logic executed by synchronization service. The routing logic, in turn, takes into account the different computing solutions subscribed to by the healthcare data source. At a step 316, the healthcare data is communicated to the processing nodes that have been determined to utilize the data. The processing nodes subsequently process the healthcare data to produce clinically-relevant outcome data that is eventually provided to, via one or more computer applications, clinicians and/or patients.

At a step 318, it is determined that one or more processing nodes associated with a second geographically-disparate data center (such as the data center 225 of FIG. 2) also subscribe to the healthcare data received from the healthcare data source. At a step 320, the healthcare data is communicated to the second data center. The second data center stores the data in association with its long-term storage data store and also communicates the healthcare data to the processing nodes that subscribe to the healthcare data. The processing nodes subsequently process the data using batch processing, low-latency processing, or both to produce clinically-relevant information.

The steps 312, 314, and 318 may be carried out substantially concurrently with each other. In other words, the healthcare data may be stored in the data center's long-term storage data store at substantially the same time as the determination of which processing nodes, both at the first data center and the second data, subscribe to the healthcare data.

The method 300 ensures that the healthcare data source need only upload the healthcare data a single time to the synchronization service. Because the healthcare data is persistently stored in at least two geographically-disparate long-term storage data stores, the healthcare data is available for later use without having to re-extract the data from the healthcare data source. For example, a new computing solution may be implemented at the first (or second) data center. The solution may be implemented in association with one or more processing nodes. Healthcare data needed by this solution can be retrieved from the first (or second) data center's long-term storage data store and processed by the new solution as opposed to having to re-extract the data from the healthcare data source.

Figure 4:
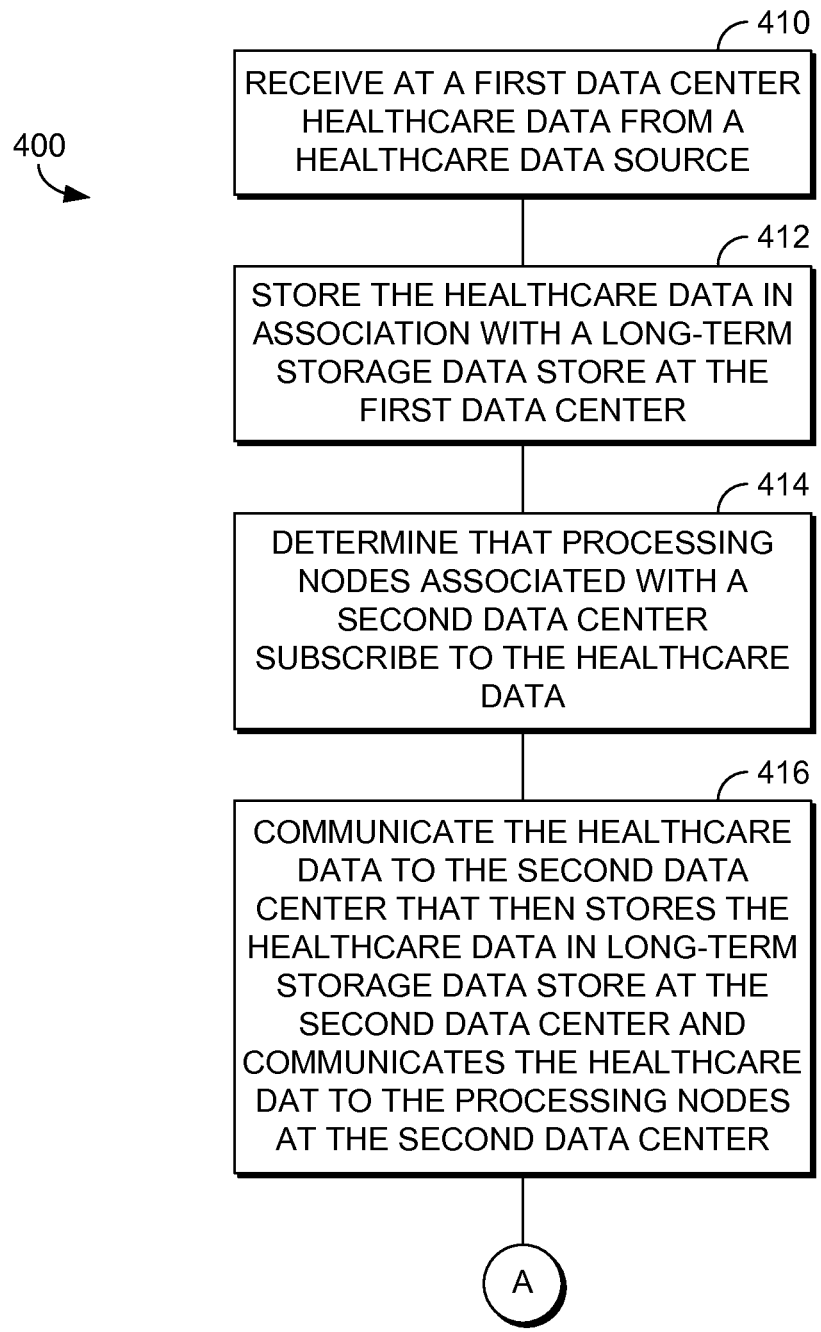

FIG. 4 depicts a flow diagram of an exemplary method 400 of synchronizing healthcare data across multiple data centers. As with the method 300, the term "step" is not meant to imply a specific order of operations. At a step 410, a piece of healthcare data is received at a first data center from a healthcare data source such as the healthcare data source 210 of FIG. 2. At a step 412, the piece of healthcare data is stored in association with a long-term storage data store located at the first data center. This holds true even if processing nodes associated with the first data center do not subscribe to the piece of healthcare data.

At a step 414, it is determined that one or more processing nodes associated with a second geographically-disparate data center subscribe to the piece of healthcare data. At a step 416, the piece of healthcare data is communicated to the second data center. The second data center subsequently stores the piece of healthcare data in association with its long-term storage data store; it also communicates the piece of healthcare data to the processing nodes that subscribe to the data. The steps 412 and 414 may be carried out substantially concurrently with each other.

As mentioned, the methods and systems outlined above are not limited to just two data centers. For example, it may be determined that one or more processing nodes associated with a third geographically-disparate processing node subscribe to the piece of healthcare data. The first data center communicates the piece of healthcare data to the third data center. The piece of healthcare data may be retrieved from the staging platform associated with the first data center. If, however, the piece of healthcare data has already been eliminated or deleted from the staging platform, it may be accessed from, for example, the long-term storage data store associated with the first or second data center and communicated to the third data center. Any and all such aspects, and any variation thereof, are contemplated as being within the scope of the invention.

Figure 5:
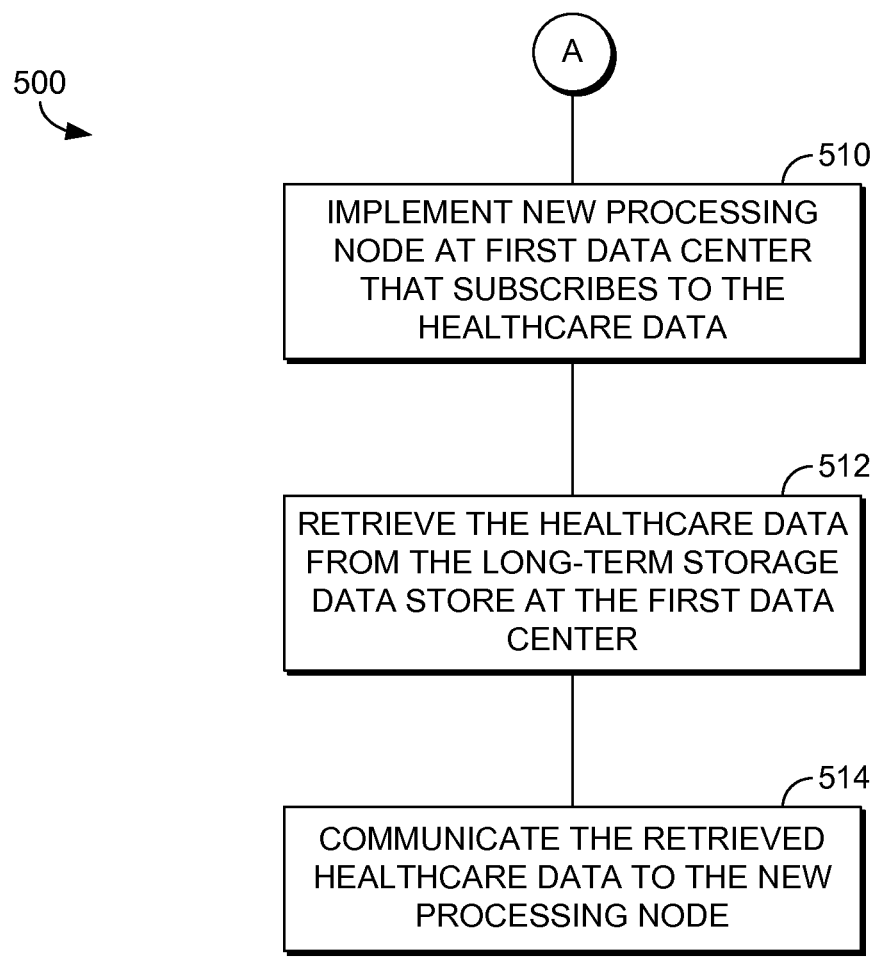

Turning to FIG. 5 which is a continuation of the method 400, at a step 510 the first data center implements a new computing solution on a processing node(s) that subscribes to the piece of healthcare data provided by the healthcare data source. At a step 512, the piece of healthcare data is retrieved from the long-term storage data store associated with the first data center. And, at a step 514, the piece of healthcare data is communicated to the processing node(s) executing the new computing solution. This eliminates the need to have to re-upload the piece of healthcare data from the healthcare data source.

As seen, the synchronization service described in this disclosure provides full disaster recovery capabilities by storing healthcare data received from a source at long-term storage data stores associated with two geographically-disparate data centers. As well, the synchronization service ensures that a healthcare data source need only upload data a single time to the service. The data is thereafter available to processing nodes across multiple disparate data centers. In addition, it is available to later-implemented solutions. This reduces the amount of processing resources expended by the healthcare data source and further keeps data center hosting costs down.

While embodiments of the present invention have been described in relation to synchronizing healthcare data across multiple, disparate data centers, embodiments will now be described as to how healthcare data is stored and managed in long-term storage associated with the data centers.

Healthcare computing solutions typically maintain their own copy of required healthcare data to perform processing and to recover from data loss. This requires storing multiple copies of the same data in different locations. A mixture of storage engines are needed to handle variations in volume and size of batches of data. The computing solutions must then sort through large amounts of stored data to access specific data required for processing. This results in excessive costs for storing healthcare data and inefficiencies in processing the healthcare data.

The current system and methods solve these problems by aggregating, partitioning, and storing healthcare data in raw form for efficient retrieval. Duplication is reduced by storing the healthcare data in centralized storage. The healthcare data is stored in organized partitions or files, allowing for efficient retrieval of only the data required by the healthcare computing solutions. This system is capable of handling a variety of payload sizes and data types while reducing the amount of storage space needed.

Figure 6:
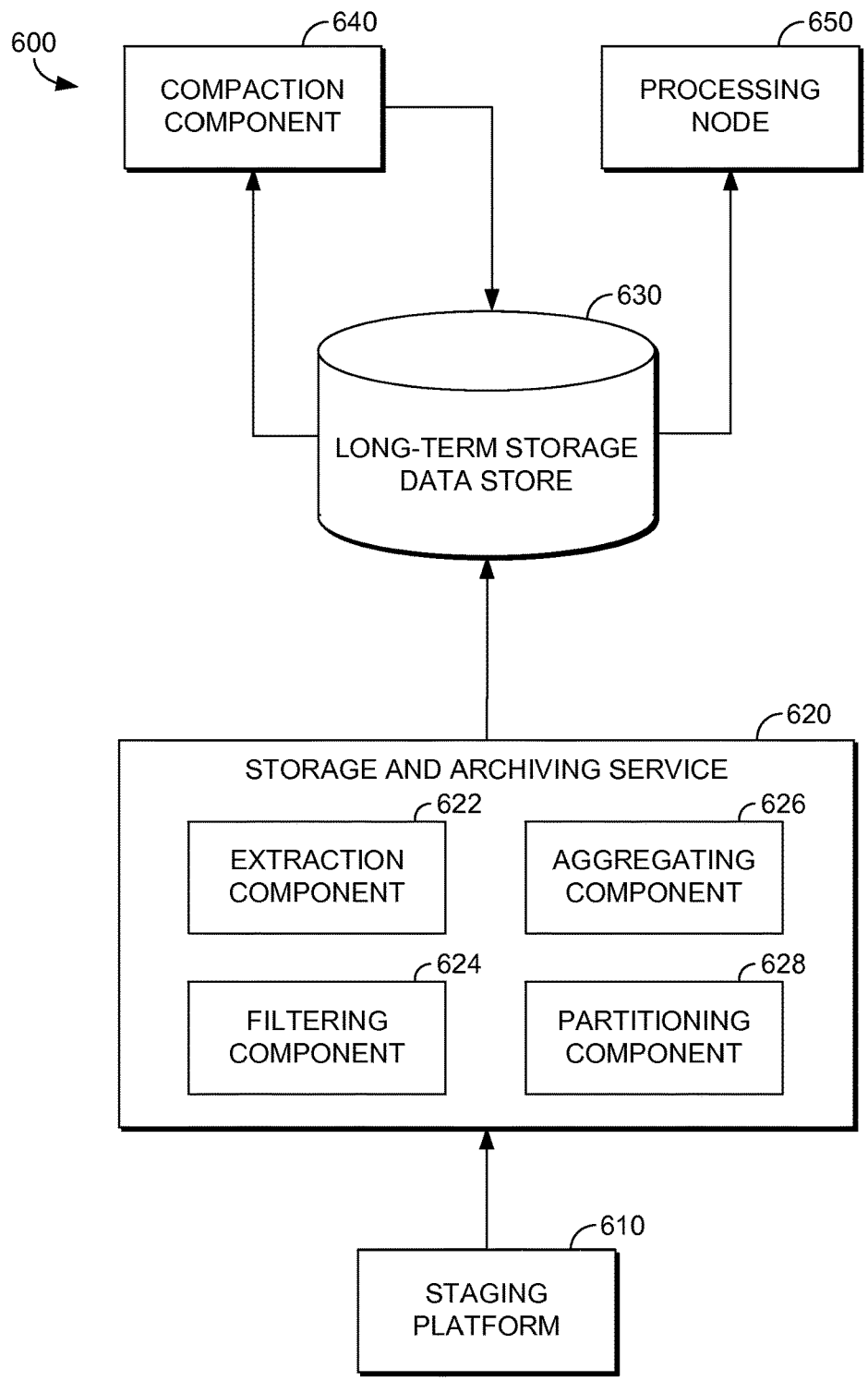
FIG. 6 is a block diagram of an exemplary computing system for aggregating, archiving, and managing healthcare data suitable to implement embodiments of the present invention.

Turning to FIG. 6, a block diagram of an exemplary computing system 600 is illustrated, in accordance with an embodiment of the present invention. FIG. 6 represents a portion of the synchronization service 205 depicted in FIG. 2. More specifically, the elements of FIG. 6 may correspond with elements 238, 248, and 254 of the first data center 215, or elements 266, 272, and 284 of the second data center 225. The system 600 is used for aggregating, archiving, and managing healthcare data. The system 600 may comprise a staging platform 610, a storage and archiving service 620, a long-term storage data store 630, a compaction component 640, and a processing node 650.

The computing system 600 is merely exemplary. For example, while the storage and archiving service 620 is illustrated as a single unit, it will be appreciated that the storage and archiving service 620 is scalable. For example, the storage and archiving service 620 may in actuality include a plurality of computing devices in communication with one another. Moreover, the long-term data store 630, or portions thereof, may be included within, for instance, the storage and archiving service 620 as a computer-storage medium. The single unit depictions are meant for clarity, not to limit the scope of embodiments in any form.

The staging platform 610 may be the same as staging platform 238 or 266 of FIG. 2. As described above, the staging platform 610 may receive healthcare data from the collector service 228. The staging platform 610 may hold a variety of data records which are identified by healthcare data source and type. Healthcare data sources may correspond with elements 210, 212, and 214 of FIG. 2, examples of which may include a hospital, a physician's office, a health information exchange, an urgent care clinic, and the like. Types of data may include, but are not limited to, information that describes various aspects of the patient state, including patient vitals, lab results, medication orders, diagnosis codes, condition codes, clinical orders, indexed values from clinical notes or other text documents, patient demographic information, patient history, patient images, and a variety of other patient information. The records may also be identified by the point in time which they were received. For instance, each incoming piece of data may be marked with a time stamp at the time it is received.

The storage and archiving service 620 takes healthcare data from the staging platform 610 and indexes the data for storage in the long-term storage data store 630. The storage and archiving service 620 may comprise an extraction component 622, an optional filtering component, an aggregating component 626, and a partitioning component 628. In some embodiments, one or more of the components 622, 624, 626, and 628 may be implemented as stand-alone applications. In other embodiments, one or more of the components 622, 624, 626, and 628, may be integrated directly into the operating system of, for example, any of the remote computers 108 or the control server 102 of FIG. 1. The components 622, 624, 626, and 628 illustrated in FIG. 6 are exemplary in nature and in number and should not be construed as limiting. Any number of components may be employed to achieve the desired functionality within the scope of embodiments hereof.

The extraction component 622 is configured to collect from the staging platform 610 one or more pieces of healthcare data from a plurality of disparate originating healthcare data sources, such as the data sources 210, 212, and 214 of FIG. 2. These originating healthcare data sources may include hospitals, clinics, health centers, or the like. Healthcare data is pulled from the staging platform 610 in an efficient manner causing minimal or no impact on the staging platform 610. This allows the staging platform 610 to continue to function to deliver data to other processing nodes for low latency processing. Extraction may occur on a periodic basis, taking batches of data from the staging platform 610 at predefined intervals, such as every hour.

The storage and archiving service 620 may optionally include a filtering component 624. The filtering component 624 filters and removes duplicate pieces of healthcare data after the healthcare data is extracted from the staging platform 610, but before the data is aggregated. This functions to reduce excess data storage usage. Generally, a piece of healthcare data will be stored in at least two locations, or data centers, for the purpose of disaster recovery. However, additional copies of the data may be unnecessary and elimination of those copies results in reduced overhead costs for storing data.

Figure 7:
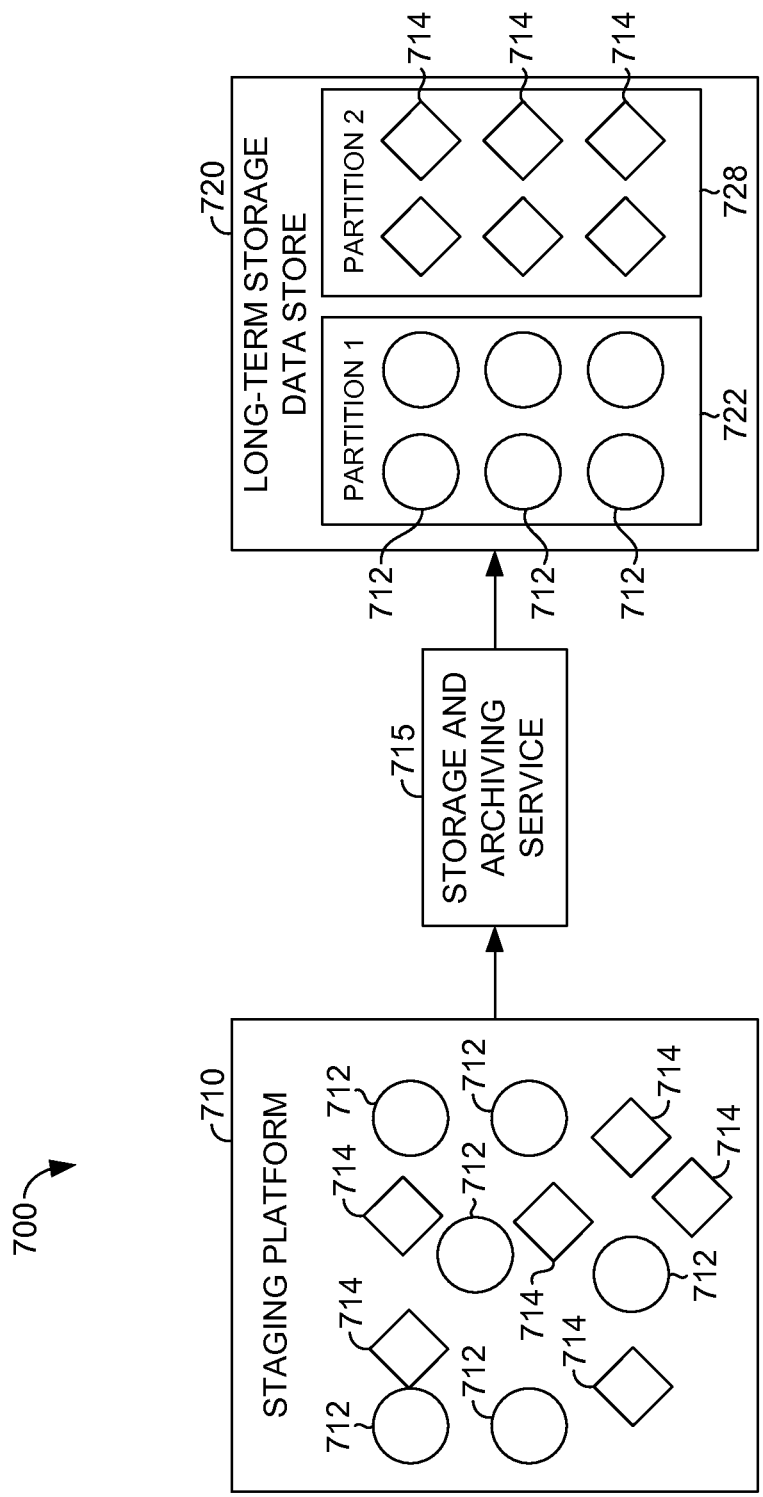
FIG. 7 is a block diagram illustrating how healthcare data is partitioned into two data types in accordance with an embodiment of the present invention.

The aggregating component 626 functions to aggregate a subset of healthcare data having the same type into batches. For example, a data source may produce multiple pieces of healthcare data of the same type in a continuous stream. These pieces of data may be, for example, pulse oximetry readings for all of the patients in the intensive care unit of a particular hospital. The aggregating component 626 collects these pieces of healthcare data into one batch. An example of the aggregation process is shown in FIG. 7, discussed further below. Aggregating similar pieces of data by type allows the system to handle a variance in the size of data payloads.

Figure 8:
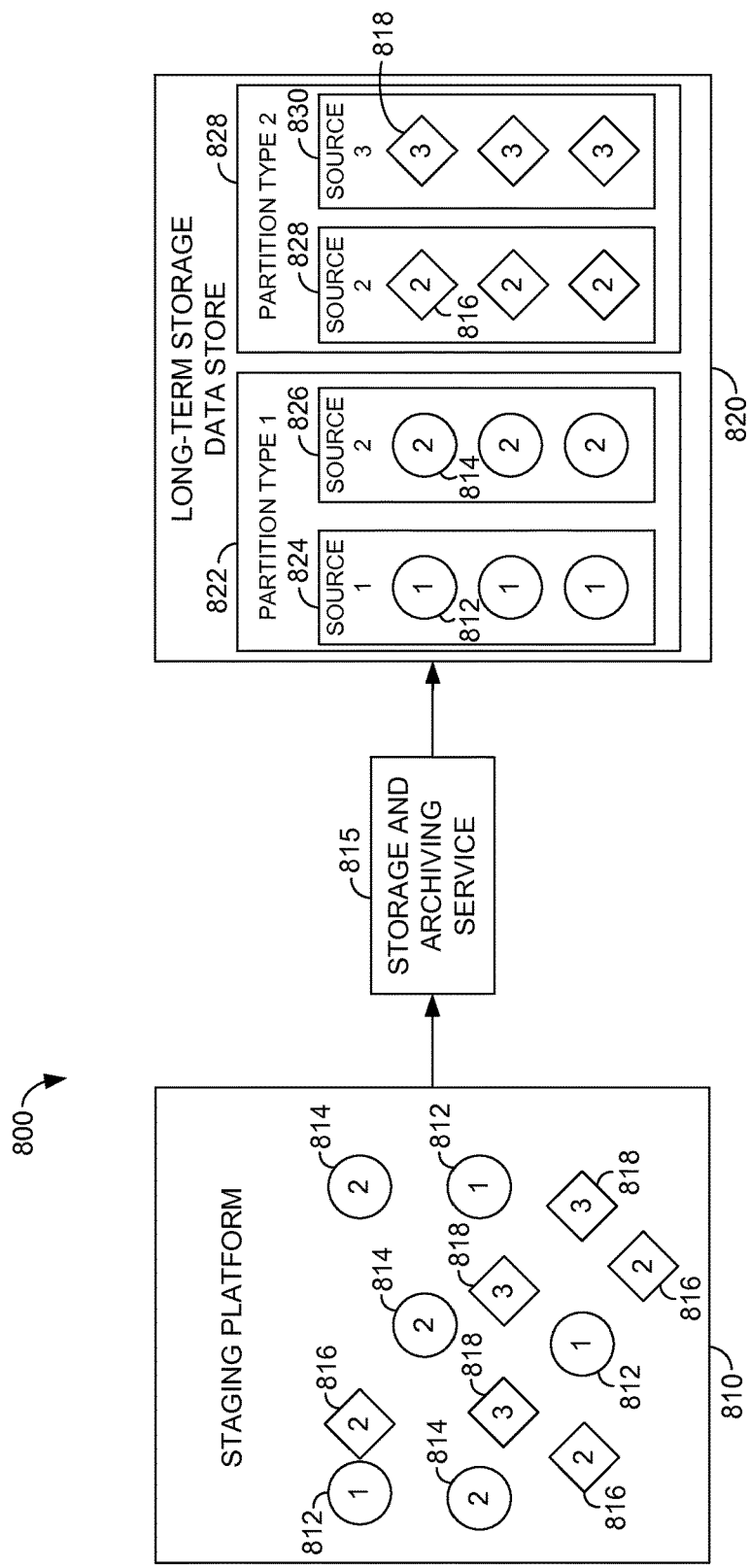
FIG. 8 is a block diagram illustrating how healthcare data is partitioned by type and source in accordance with an embodiment of the present invention.

The partitioning component 628 serves to sort the healthcare data by originating healthcare data source. As is shown in FIG. 8, after pieces of healthcare data have been aggregated by type, the data may then be partitioned by source. Alternatively, the system may simultaneously aggregate and partition the pieces of healthcare data by type and source. For example, prescription records for all patients of the cardiology department of a given hospital could be aggregated and partitioned together. This multi-level partitioning strategy allows for efficient access to any combination of data needed for various processing needs without sorting through unnecessary data. Without the multi-level partitioning, a processing node would need to inefficiently process every piece of healthcare data regardless of its value to the computing solution that is requesting the data.

In one embodiment, the partitioning component 628 may further sort the healthcare data into time slices based on when the healthcare data was received. This allows a processing node to easily access recent data or obtain data from a particular time period. For example, a processing node may request access to all pulse oximetry readings from the county hospital taken in the last hour. The time slices may include data from a range of time periods. For example, a time slice could include all data from a time period lasting one minute, one hour, one day, one week, one month, one year, and so on. Storing recent data separate from older data allows for more efficient processing of data by solutions that subscribe to batches of recently acquired data.

After the healthcare data has been extracted, aggregated, and partitioned, the healthcare data is stored in a long-term storage data store 630. Because the data is stored in partitions based on type and source, it may be efficiently accessed at a later time for processing by one or more processing nodes 650. The healthcare data is stored in raw form so that the data may be utilized by various computing solutions.

Computing solutions may send requests from one or more processing nodes, such as processing node 650 of FIG. 6, to the long-term storage data store 630. The request may be for specific subsets of healthcare data having a certain type and/or source. The request may further specify a time frame for when the data was received. In response to the request from a processing node 650, the long-term storage data store 630 accesses the requested healthcare data and delivers the data to the processing node 650. The computing solution may then process the exact data it requires to generate a clinically relevant outcome. By reducing the amount of data that a computing solution needs to sort through to obtain the required data, processing speeds are improved and the computing solutions can perform more efficiently.

The compaction component 640 works in conjunction with the long-term storage data store 630 to optionally compact multiple older time slices into larger slices. This reduces the needed storage space in the long-term storage data store 630, thus saving on storage costs. This may be done automatically on a regular basis to combine older data into a more efficient storage format. For example, after 24 hours has passed since data has been stored, all one-hour time slices may be compacted into 12 hour slices. The usefulness of storing separate time slices diminishes over time, making it more efficient to store data in larger batches. For example, multiple separate files may be combined into a single file. This allows the physical storage of data to evolve based on new or evolving processing needs such as new partitioning strategies or supporting new use cases. Regular compaction of time slices of data results in lower overhead for storage space as maintaining separate time slices places a burden on the storage engine.

Turning now to FIG. 7, a block diagram 700 is illustrated, in accordance with an embodiment of the present invention, showing the partitioning of healthcare data into two data types. The staging platform 710 may collect more than one type of data from a single source. Shown here, there are pieces of data of a first type 712 and pieces of data of a second type 714. For example, the data of a first type 712 may be blood pressure readings while data of a second type 714 may be glucose meter readings. These pieces of data are aggregated by type by the storage and archiving service 715 and stored in separate partitions, a first partition 722 and a second partition 728, within the long-term storage data store 720. The partitions may separate the pieces of data physically, or the data may be separated conceptually. For example, the pieces of data may be stored in a virtual file system in which a user sees a consolidated view consisting of a hierarchy of folders, but in fact the data is distributed across multiple storage machines in disparate locations.

FIG. 8 depicts a block diagram 800 representing the partitioning of healthcare data by type and source. In this example, pieces of data of a first type from a first source 812, pieces of data of a first type from a second source 814, pieces of data of a second type from a second source 816, and pieces of data of a second type from a third source 818 are all collected at the staging platform 810. For example, the staging platform could collect HL7 files from Hospital A, HL7 files from Hospital B, glucose meter readings from Hospital B, and glucose meter readings from Clinic C. The pieces of data are then aggregated by type by the storage and archiving service 815, such that pieces of data of the first type 812, 814 are stored in a first partition 822 and pieces of data of the second type 816, 818 are stored in a second partition 828 within a long-term storage data store 920. The pieces of data are further partitioned by source by the storage and archiving service 815. As shown in FIG. 8, pieces of data of a first type are partitioned such that a first type first source partition 824 stores pieces of data of the first type from the first source 812 and a first type second source partition 826 stores pieces of data of the first type from the second source 814. Similarly, pieces of a data of a second type are partitioned such that a second type second source partition 828 stores pieces of data of the second type from the second source 816 and a second type third source partition 830 stores pieces of data of the second type from the third source 818. To continue with the example above, HL7 files from Hospital A would be stored in the first type first source partition, HL7 files from Hospital B would be stored in the first type second source partition, glucose meter readings from Hospital B would be stored in the second type second source partition, and glucose meter readings from Clinic C would be stored in the second type third source partition. This multi-level partitioning strategy allows access to any combination of healthcare data, allowing processing nodes to easily and efficiently process pertinent healthcare data.

Figure 9:
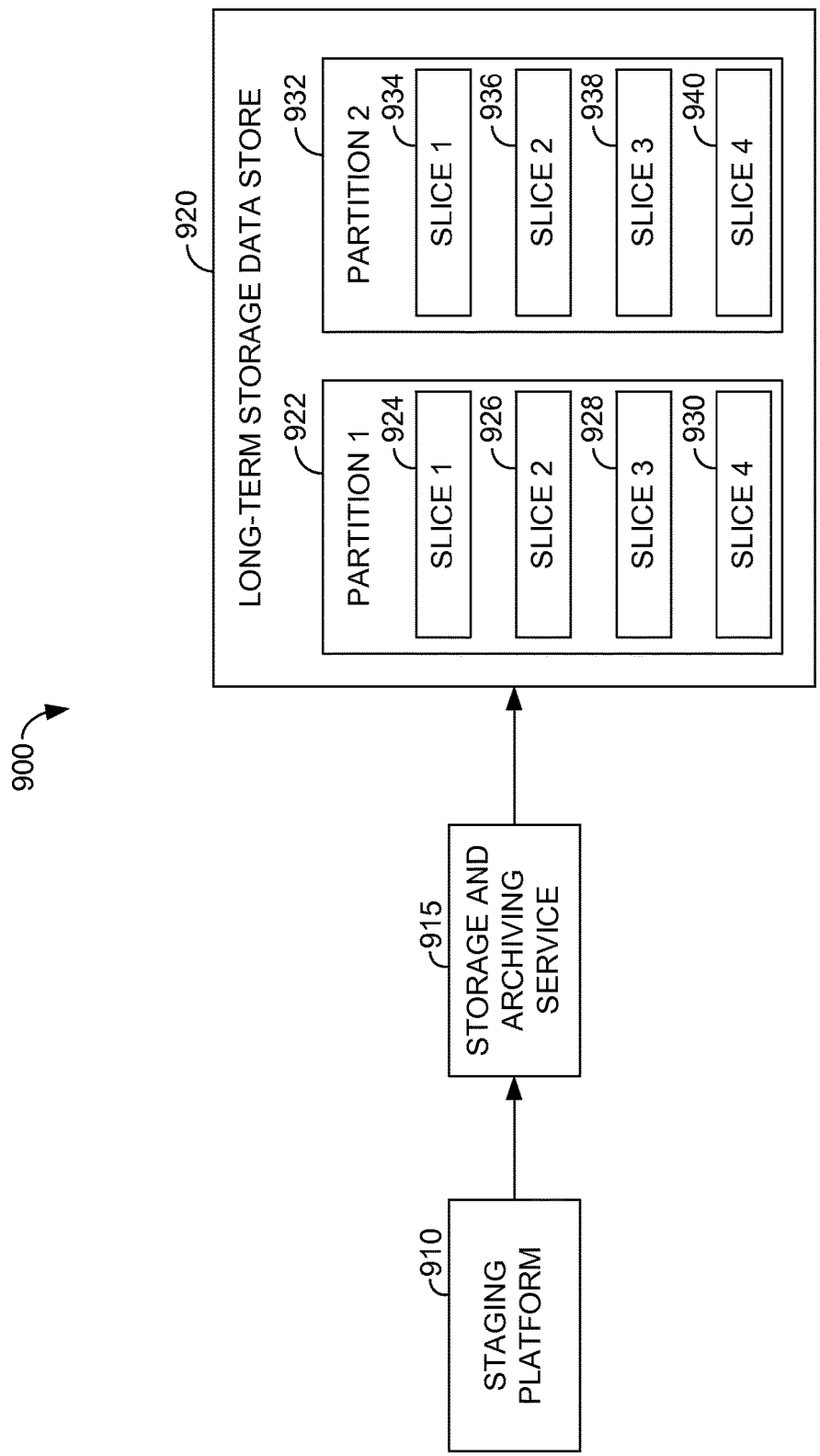
FIG. 9 is a block diagram illustrating how healthcare data is partitioned based on when the healthcare data was received in accordance with an embodiment of the present invention.

FIG. 9 illustrates a block diagram 900 representing the partitioning of healthcare data by the time the healthcare data was received. Healthcare data gathered in the staging platform 910 is partitioned into a first partition 922 or second partition 932 within a long-term storage data store based on type and/or source by the storage and archiving service 915. The healthcare data is then further partitioned into time slices. For example, data within the first partition 922 may be separated into a first slice 924, a second slice 926, a third slice 928, and a fourth slice 930. Similarly, data within the second partition 932 is separated into a first slice 934, a second slice 936, a third slice 938, and a fourth slice 940. The time slices may be organized by how recently the data was received. For example, the first slice 924 may contain data collected an hour ago, the second slice 926 two hours ago, the third slice 928 three hours ago, and the fourth slice 930 four hours ago.

Figure 10:
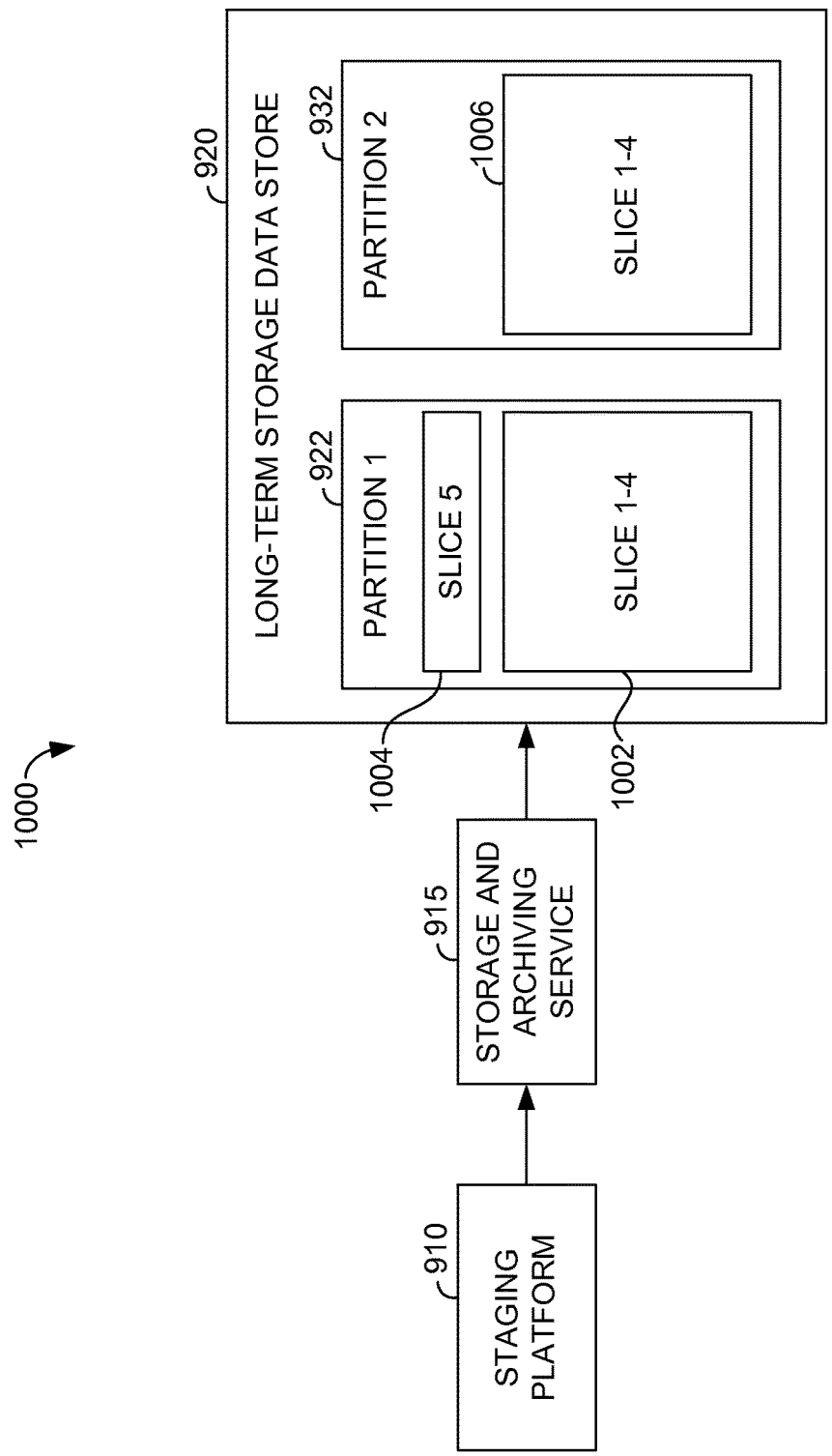
FIG. 10 is a block diagram illustrating how multiple time slices are compacted into a larger historic data slice in accordance with an embodiment of the present invention.

In FIG. 10, a block diagram 1000 depicts the compaction of the multiple time slices 924, 926, 928, and 930 of FIG. 9 into a larger first historic data slice 1002. Compaction may be performed by a compaction component, such as compaction component 640 of FIG. 6. A new batch of data is stored in a fifth data slice 1004. Following the same example of FIG. 9, the fifth data slice 1004 contains data collected an hour ago and the first historic data slice 1002 may contain data collected between two and five hours ago. The individual time slices 934, 936, 938, and 940 of FIG. 9 within the second partition 932 have also been compacted into a second historic data slice 1006. However, no new data has entered the second partition 932 since the compaction has occurred.

Figure 11:
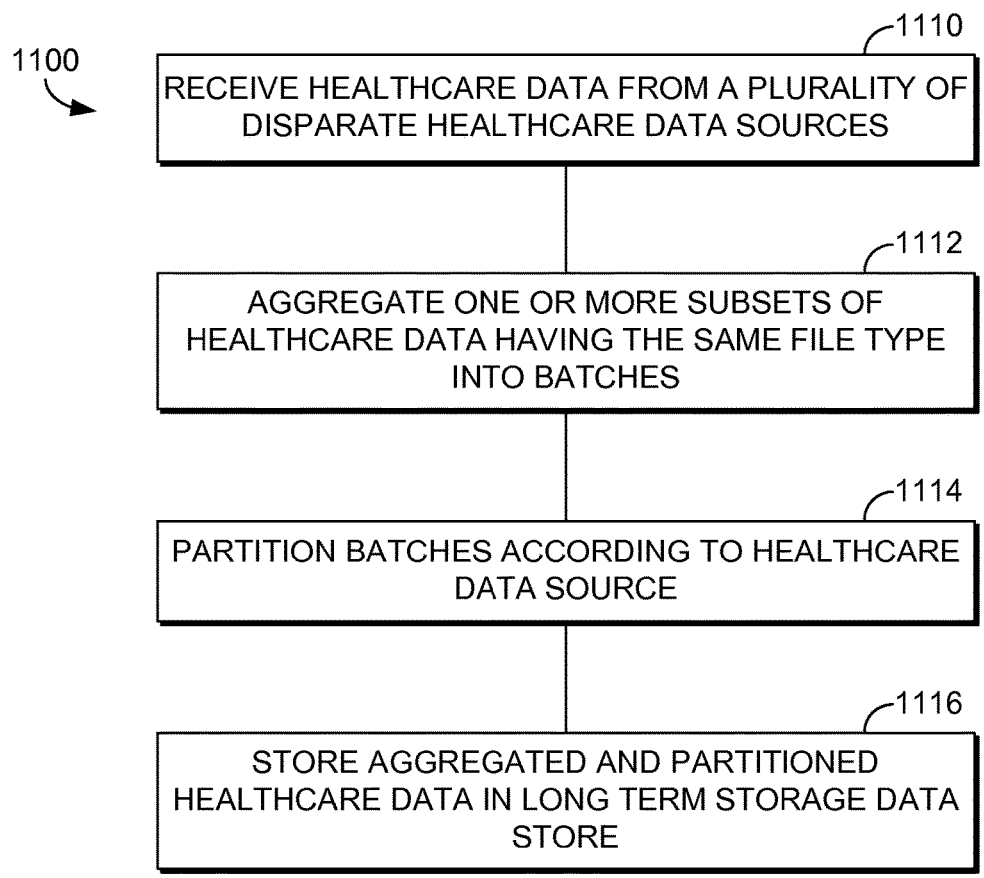
FIG. 11 is a flow diagram of an exemplary method of aggregating, partitioning, and storing raw healthcare data for efficient retrieval in accordance with an embodiment of the present invention.

Turning now to FIG. 11, a flow diagram is depicted of an exemplary method 1100 of aggregating, partitioning, and storing raw healthcare data for efficient retrieval. The method may be carried out by a storage and archiving service, such as the storage and archiving service 620 of FIG. 6, within a data center, such as the data center 225 of FIG. 2. At step 1110, healthcare data is received from a plurality of disparate heathcare data sources. For example, these healthcare data sources may be the data sources 210, 212, 214 depicted in FIG. 2. As mentioned previously, the healthcare data may be collected from the healthcare data sources by a collector service, such as the collector service 228, and then communicated to a staging platform, such as staging platform 266. The data may then be extracted from the staging platform and received by a storage and archiving service. For example, the extraction component 622 of the storage of archiving service 620 of FIG. 6 may extract the data.

At this point, one or more pieces of duplicate healthcare data may be filtered and removed by a filtering component, such as the filtering component 624 of FIG. 6. This is done to remove unnecessary duplicate copies of data in order to reduce the amount of storage space required to house the healthcare data, thus reducing costs.

At step 1112, one or more subsets of healthcare data is aggregated into batches having the same file type by an aggregating component such as the aggregating component 626 of FIG. 6. An example of aggregating healthcare data by type is depicted in FIG. 7. At step 1114, the batches of healthcare data aggregated by data type are then partitioned according to the healthcare data source they were received from by a partitioning component such as the partitioning component 628 of FIG. 6. An example of partitioning healthcare data by source is depicted in FIG. 8.

The healthcare data may be further partitioned into slices based on the time that the healthcare data was received. An example of partitioning healthcare data into time slices is depicted in FIG. 9. The time slices may cover specific time ranges such as one minute, one hour, one day, one week, one month, or one year. This enables processing nodes to select to receive the most recent data collected in a given time. Alternatively, the processing node could request a batch of historic data for processing in a new computing solution. These time slices may be compacted into larger slices to reduce storage space after a certain amount of time has passed.

At step 1118, the aggregated and partitioned healthcare data is stored in a long-term storage data store, such as long-term storage data store 630 in FIG. 6 or 272 in FIG. 2. The healthcare data may be stored, for example, in a virtual file system.

If the healthcare data has been stored in time slices, as depicted in FIG. 9, the time slices may later be compacted, as shown in FIG. 10. Multiple time slices that have been stored for a given period of time may be compacted into larger slices, by a compacting component such as compaction component 640 of FIG. 6, in order to reduce the amount of storage space required to house the healthcare data.

Figure 12:
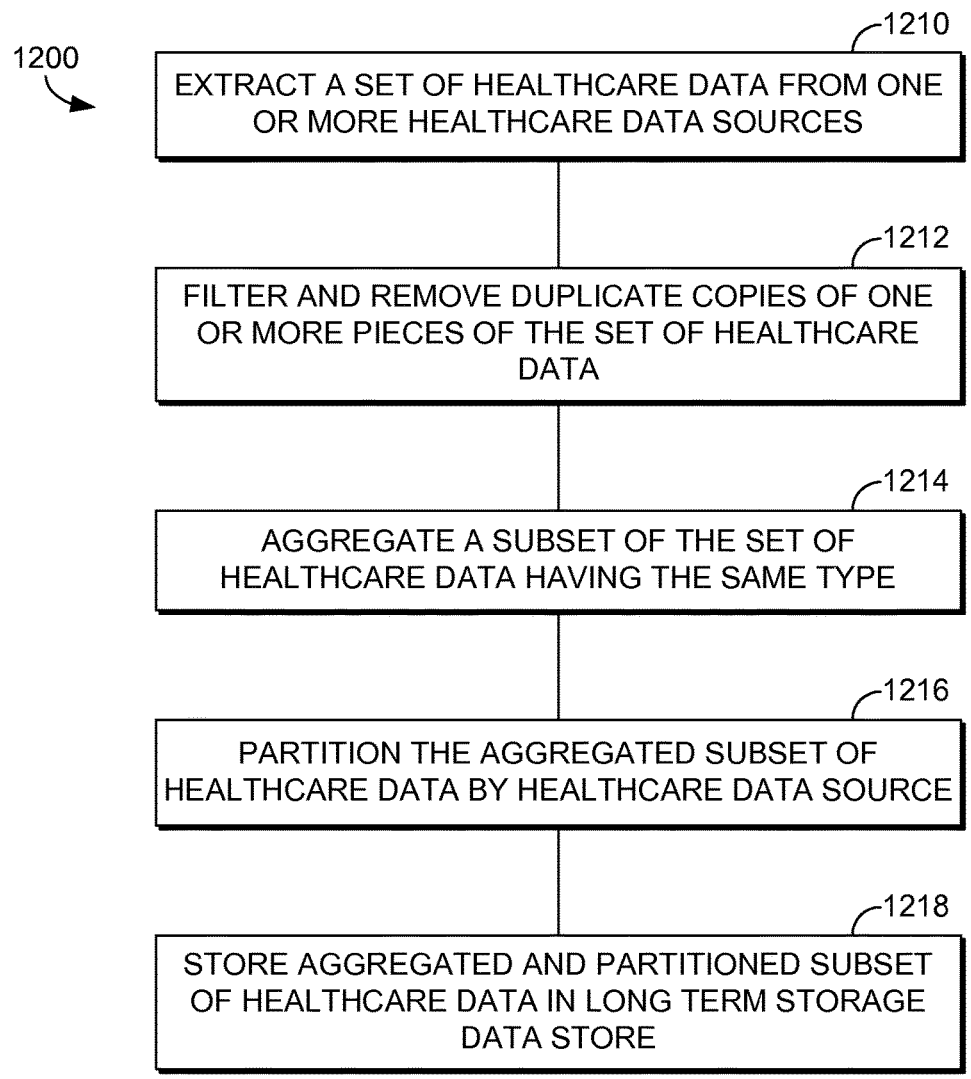
FIG. 12 is a flow diagram of an exemplary method of aggregating, partitioning, and storing healthcare data in accordance with an embodiment of the present invention.

FIG. 12 depicts a flow diagram of an exemplary method 1200 of aggregating, partitioning, and storing healthcare data. At step 1210, a set of healthcare data is extracted from one or more healthcare data sources. The healthcare data may be extracted by an extraction component, such as extraction component 622 of FIG. 6, from a staging platform, such as staging platform 610 of FIG. 6, which has gathered data from one or more data sources such as data sources 210, 212, 214 in FIG. 2. Pieces of healthcare data of the set of healthcare data may be of varying file sizes. The pieces of healthcare data may be labeled with metadata to identify type, healthcare data source, and the time the data was received.

At step 1212, duplicate copies of one or more pieces of the set of healthcare data are filtered and removed by a filtering component, such as filtering component 624 of FIG. 6. This functions to eliminate excess copies of healthcare data that do not need to be stored, thus saving storage space. At step 1214, a subset of the set of healthcare data having the same type is aggregated by an aggregating component, such as aggregating component 626 of FIG. 6. At step 1216, the aggregated subset of healthcare data is partitioned by healthcare data source by a partitioning component, such as partitioning component 628 of FIG. 6. The aggregated and partitioned subset of healthcare data may be further partitioned into time slices based on a time the healthcare data was received.

At step 1218, the aggregated and partitioned subset of healthcare data is stored in a long-term storage data store such as long-term storage data store 630 of FIG. 6. The healthcare data may be stored in a hierarchy of folders based on type and healthcare data source. After a given amount of time has passed, old time slices of data may be compacted into larger slices by a compaction component, such as compaction component 640 of FIG. 6. Compaction reduces the amount of storage space needed to house the data. For example, multiple time slice files may be combined into a single file, thus requiring less physical space for storage.

Figure 13:
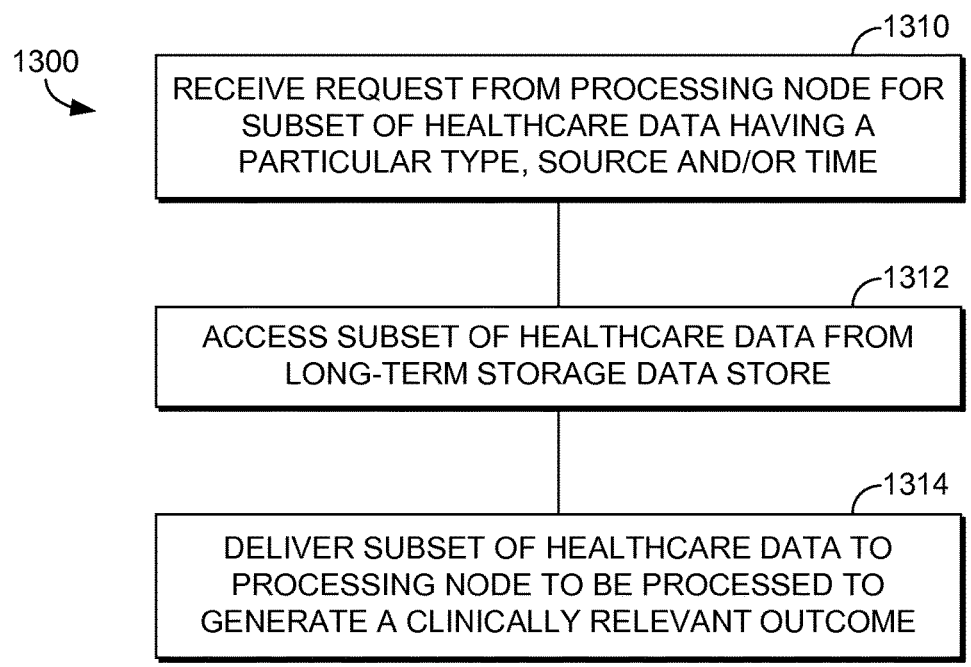
FIG. 13 is a flow diagram of an exemplary method of accessing stored healthcare data in accordance with an embodiment of the present invention.

FIG. 13 depicts a method 1300 of accessing stored healthcare data, which may occur after either method 1100 or 1200. At step 1310, a long-term storage data store receives a request from a processing node for a subset of healthcare data having a particular type, source, and/or time. For example, the processing node may be processing node 284 in FIG. 2 or 650 in FIG. 6. The processing node may be configured to perform batch processing of healthcare data. The request may be, for example, for a subset of data from a given list of sources. For example, the list of sources could include all clinics associated with Hospital A in Dallas. The request may also be for all available data of a given type. For instance, the request could be for all HL7 files. The request may also be for all data from a list of given sources of a certain type that were received in a given amount of time, such as the last 24 hours.

The subset of healthcare data is then accessed from the long-term storage data store in step 1312. The long-term storage data store may be long-term storage data store 272 in FIG. 2 or 630 in FIG. 6. In step 1314 the subset of healthcare data is delivered to the processing node where it is processed to generate a clinically relevant outcome. For example, glucose meter readings may be processed to generate a list of patients at risk for developing diabetes.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized method carried out by at least one server having at least one processor for aggregating, partitioning, and storing raw healthcare data for efficient retrieval, the method comprising:
    receiving, at a staging platform associated with a first data center, healthcare data from a plurality of disparate healthcare data sources of a distributed computing environment;
    implementing a multi-level partitioning strategy for efficient access to a plurality of healthcare data batches, the multi-level partitioning strategy eliminating the need to process healthcare data that is not required for a computing solution, wherein the multi-level partitioning strategy comprises:
        (A) aggregating, using the at least one processor, one or more subsets of the healthcare data having the same file type into batches; and
        (B) partitioning the batches according to healthcare data source in order to handle a variety of payload sizes and data types while reducing an amount of storage needed;
    storing the healthcare data batches in a long term storage data store associated with a second data center of the plurality of disparate data centers of the distributed computing environment;
    receiving a request from a processing node for at least one of the healthcare data batches;
    accessing the at least one requested healthcare data batches from the long-term storage data store; and
    delivering the at least one requested healthcare data batches, where the at least one requested healthcare data batches is processed to generate clinically relevant outcome information.

2. The method of claim 1, further comprising, prior to aggregating the one or more subsets of healthcare data, filtering and removing one or more pieces of duplicate healthcare data.

3. The method of claim 1, wherein the processing node performs batch processing of data.

4. The method of claim 1, wherein the long-term storage data store stores the healthcare data in a virtual file system.

5. The method of claim 1, further comprising partitioning healthcare data in slices based on a time when the healthcare data was received.

6. The method of claim 5, wherein the slices contain data for one of the following time periods:
    one minute,
    one hour,
    one day,
    one week,
    one month, or
    one year.

7. The method of claim 5, further comprising compacting multiple time slices that have been stored for a given period of time into larger slices to reduce storage space.

8. A computer-implemented system for aggregating, archiving, and managing healthcare data, the computer-implemented system comprising:
    one or more disparate originating healthcare data sources;
    one or more processing nodes;
    a staging component that receives and indexes one or more pieces of healthcare data from a plurality of disparate originating healthcare data sources so that it is optimized for low-latency processing by storing the data in a raw form with additional metadata describing a source and a time received for the data;
    an extraction component that extracts one or more pieces of healthcare data received and indexed at the staging component from a plurality of disparate originating healthcare data sources;
    an aggregating component that aggregates a subset of the healthcare data extracted by the extraction component, the aggregating component aggregating the subset of healthcare data having the same type into batches;
    a partitioning component that sorts the batches by originating healthcare data source; and
    a long-term storage data store for storing the batches;
    wherein the staging component further receives a request from the one or more processing nodes for at least one of the batches;
    wherein the staging component further accesses the at least one of the batches in the long-term storage data store; and
    wherein the staging component further delivers the at least one of the batches of healthcare data to the processing node where the at least one of the requested batches will be processed to produce a clinically relevant outcome.

9. The system of claim 8, further comprising a filtering component that filters and removes duplicate pieces of healthcare data.

10. The system of claim 8, wherein the partitioning component further sorts the healthcare data into time slices based on when the healthcare data was received.

11. The system of claim 10, further comprising a compaction component that compacts multiple older time slices into larger slices to reduce needed storage space in the long-term storage data store.

12. The system of claim 8 wherein the plurality of disparate originating healthcare data sources include hospitals, clinics, or health centers.

13. One or more non-transitory computer-storage media having computer-executable instructions embodied thereon that, when executed, perform a method of aggregating, partitioning, and storing healthcare data, the method comprising:
    extracting a set of healthcare data from one or more healthcare data sources;
    filtering and removing duplicate copies of one or more pieces of the set of healthcare data;
    aggregating a subset of the set of healthcare data having the same type;
    partitioning the aggregated subset of healthcare data by healthcare data source; and
    storing the aggregated and partitioned subset of healthcare data in one or more long-term storage data stores;

receiving a request from a processing node for a batch of healthcare data of a particular type and healthcare data source; and accessing the batch of healthcare data in the long-term storage data store; and delivering the batch of healthcare data to the processing node where the requested batch of healthcare data will be processed to produce a clinically relevant outcome.

14. The media of claim 13, further comprising labeling each piece of healthcare data of the set of healthcare data with metadata identifying the time the piece of healthcare data was received and further partitioning the aggregated subset of healthcare data into time slices based on a time the healthcare data was received.

15. The media of claim 14, further comprising compacting older time slices of data into larger slices such that the data requires less physical space for storage.

16. The media of claim 13, wherein the request further specifies a time period for the batch of healthcare data.

17. The method of claim 13, wherein the aggregated and partitioned subset of healthcare data is stored in a hierarchy of folders based on type and healthcare data source.

18. The method of claim 13, wherein the pieces of healthcare data of the set of healthcare data are of varying file sizes.

* * * * *